(12) United States Patent
Royster, Jr. et al.

(10) Patent No.: US 7,462,405 B2
(45) Date of Patent: Dec. 9, 2008

(54) ORGANIC ELEMENT FOR ELECTROLUMINESCENT DEVICES

(75) Inventors: Tommie L. Royster, Jr., Rochester, NY (US); David J. Giesen, Webster, NY (US); Adam Freeman, Penfield, NY (US)

(73) Assignee: Eastman Kodak Company, Rochester, NY (US)

( * ) Notice: Subject to any disclaimer, the term of this patent is extended or adjusted under 35 U.S.C. 154(b) by 536 days.

(21) Appl. No.: 10/974,264

(22) Filed: Oct. 27, 2004

(65) Prior Publication Data

US 2005/0136286 A1 Jun. 23, 2005

Related U.S. Application Data

(63) Continuation-in-part of application No. 10/729,325, filed on Dec. 5, 2003, now abandoned.

(51) Int. Cl.
*H01L 51/50* (2006.01)
*C09K 11/06* (2006.01)

(52) U.S. Cl. .................. 428/690; 428/917; 313/504; 313/506; 257/98; 556/58; 252/301.16

(58) Field of Classification Search ............. 428/690, 428/917; 313/504, 506, 112; 257/98; 556/58; 252/301.16
See application file for complete search history.

(56) References Cited

U.S. PATENT DOCUMENTS 5,061,569 A * 10/1991 VanSlyke et al. .......... 428/457
6,641,933 B1 * 11/2003 Yamazaki et al. ......... 428/690
2005/0230665 A1 * 10/2005 Thompson ................ 252/500

FOREIGN PATENT DOCUMENTS

| EP | 1 245 659 | 10/2002 |
|----|-----------|---------|
| WO | 03/066067 | 8/2003 |
| WO | 03/076549 | 9/2003 |
| WO | 03/079737 | 9/2003 |

OTHER PUBLICATIONS

Lam et al., Macromolecules, (2002), 35, p. 1229-1240.*
Wu et al., Organometallics (1993), vol. 12, p. 3971-3978.*
Arnold et al., Organometallics (1988), vol. 7, p. 2261-2266.*
Kunkely et al., Transition Metal Chemistry, vol. 25, (2000), p. 234-236.*
X. Xu, et al., "Electrochemical Oxidation and Nucleophillic Addition Reactions of Metallocenes in Electrospray Mass Spectrometry", Analytical Chemistry, vol. 66, No. 1, Jan. 1, 1994, pp. 119-125.
T. W. Spradau, et al., "Preparation of Cyclopentadienyltricarbonylrhenium Complexes Using a Double Ligand-Transfer Reaction", Organometallics, 1998, pp. 2009-2017.
Y. Li, et al., "Carbonyl polypyridyl Re(I) complexes as organic electroluminescent materials", Synthetic Metals, 1999, pp. 257-260.
J. A. Crayston, et al., Journal of Organometallic Chemistry, 423 (1992), pp. 223-239.
E. M. Kober, et al., J. Phys. Chem., 1986, 90, pp. 3722-3734.
T. J. Meyer, et al., Inorg. Chem. 1995, 34, pp. 473-487.
Pei-Chi Wu, et al., "Synthesis and Characterization of Metal Complexes Possessing the 5-(2-Pyridyl) Pyrazolate Ligands: The Observation of Remarkable Osmium-Induced Blue Phosphorescence in Solution at Room Temperature", 2003, pp. 4938-4946.

* cited by examiner

*Primary Examiner*—Dawn Garrett
(74) *Attorney, Agent, or Firm*—Arthur E. Kluegel

(57) ABSTRACT

Disclosed is an electroluminescent device comprising a light-emitting layer containing a light emitting phosphorescent material that contains an organometallic complex comprising a metal selected from the group consisting of Mo, W, Re, Ru, and Os that is coordinated to a neutral or negatively-charged ligand group through the π electrons of the ligand with a hapticity greater than 2. The device provides useful light emissions.

44 Claims, 1 Drawing Sheet

ORGANIC ELEMENT FOR ELECTROLUMINESCENT DEVICES

This application is a continuation-in-part of U.S. Ser. No. 10/729,325 filed Dec. 5, 2003, now abandoned, entitled "Organic Element for Electroluminescent Devices."

FIELD OF THE INVENTION

This invention relates to an electroluminescent device comprising a light-emitting layer containing a light emitting phosphorescent material that contains an organometallic complex comprising a metal selected from the group consisting of Mo, W, Re, Ru, and Os that is coordinated to a neutral or negatively-charged ligand group through the π electrons of the ligand with a hapticity greater than 2.

BACKGROUND OF THE INVENTION

While organic electroluminescent (EL) devices have been known for over two decades, their performance limitations have represented a barrier to many desirable applications. In simplest form, an organic EL device is comprised of an anode for hole injection, a cathode for electron injection, and an organic medium sandwiched between these electrodes to support charge recombination that yields emission of light. These devices are also commonly referred to as organic light-emitting diodes, or OLEDs. Representative of earlier organic EL devices are Gurnee et al. U.S. Pat. No. 3,172,862, issued Mar. 9, 1965; Gurnee U.S. Pat. No. 3,173,050, issued Mar. 9, 1965; Dresner, "Double Injection Electroluminescence in Anthracene", RCA Review, Vol. 30, pp. 322-334, 1969; and Dresner U.S. Pat. No. 3,710,167, issued Jan. 9, 1973. The organic layers in these devices, usually composed of a polycyclic aromatic hydrocarbon, were very thick (much greater than 1 µm). Consequently, operating voltages were very high, often >100V.

More recent organic EL devices include an organic EL element consisting of extremely thin layers (e.g. <1.0 µm) between the anode and the cathode. Herein, the term "organic EL element" encompasses the layers between the anode and cathode electrodes. Reducing the thickness lowered the resistance of the organic layer and has enabled devices that operate much lower voltage. In a basic two-layer EL device structure, described first in U.S. Pat. No. 4,356,429, one organic layer of the EL element adjacent to the anode is specifically chosen to transport holes, therefore, it is referred to as the hole-transporting layer, and the other organic layer is specifically chosen to transport electrons, referred to as the electron-transporting layer. Recombination of the injected holes and electrons within the organic EL element results in efficient electroluminescence.

There have also been proposed three-layer organic EL devices that contain an organic light-emitting layer (LEL) between the hole-transporting layer and electron-transporting layer, such as that disclosed by Tang et al [*J. Applied Physics*, 65, 3610-3616, (1989)]. The light-emitting layer commonly consists of a host material doped with a guest material Still further, there has been proposed in U.S. Pat. No. 4,769,292 a four-layer EL element comprising a hole-injecting layer (HIL), a hole-transporting layer (HTL), a light-emitting layer (LEL) and an electron transport/injection layer (ETL). These structures have resulted in improved device efficiency.

Many emitting materials that have been described as useful in an OLED device emit light from their excited singlet state by fluorescence. The excited singlet state is created when excitons formed in an OLED device transfer their energy to the excited state of the dopant. However, it is generally believed that only 25% of the excitons created in an EL device are singlet excitons. The remaining excitons are triplet, which cannot readily transfer their energy to the singlet excited state of a dopant. This results in a large loss in efficiency since 75% of the excitons are not used in the light emission process.

Triplet excitons can transfer their energy to a dopant if it has a triplet excited state that is low enough in energy. If the triplet state of the dopant is emissive it can produce light by phosphorescence, wherein phosphorescence is a luminescence involving a change of spin state between the excited state and the ground state. In many cases singlet excitons can also transfer their energy to lowest singlet excited state of the same dopant. The singlet excited state can often relax, by an intersystem crossing process, to the emissive triplet excited state. Thus, it is possible, by the proper choice of host and dopant, to collect energy from both the singlet and triplet excitons created in an OLED device and to produce a very efficient phosphorescent emission.

One class of useful phosphorescent materials are transition metal complexes having a triplet excited state. For example, fac-tris(2-phenylpyridinato-N,$C^{2'}$)iridium(III) ($Ir(ppy)_3$) strongly emits green light from a triplet excited state owing to the large spin-orbit coupling of the heavy atom and to the lowest excited state which is a charge transfer state having a Laporte allowed (orbital symmetry) transition to the ground state (K. A. King, P. J. Spellane, and R. J. Watts, *J. Am. Chem. Soc.*, 107, 1431 (1985), M. G. Colombo, T. C. Brunold, T. Reidener, H. U. Gudel, M. Fortsch, and H.-B. Burgi, *Inorg. Chem.*, 33, 545 (1994) Small-molecule, vacuum-deposited OLEDs having high efficiency have also been demonstrated with $Ir(ppy)_3$ as the phosphorescent material and 4,4'-N,N'-dicarbazole-biphenyl (CBP) as the host (M. A. Baldo, S. Lamansky, P. E. Burrows, M. E. Thompson, S. R. Forrest, *Appl. Phys. Lett.*, 75, 4 (1999), T. Tsutsui, M.-J. Yang, M. Yahiro, K. Nakamura, T. Watanabe, T. Tsuji, Y. Fukuda, T. Wakimoto, S. Miyaguchi, Jpn. *J. Appl. Phys.*, 38, L1502 (1999)).

Another class of phosphorescent materials include compounds having interactions between atoms having $d^{10}$ electron configuration, such as $Au_2(dppm)Cl_2$ (dppm=bis(diphenylphosphino)methane) (Y. Ma et al, *Appl. Phys. Lett.*, 74, 1361 (1998)). Still other examples of useful phosphorescent materials include coordination complexes of the trivalent lanthanides such as $Tb^{3+}$ and $Eu^{3+}$ (J. Kido et al, *Appl. Phys. Lett.*, 65, 2124 (1994)). While these latter phosphorescent compounds do not necessarily have triplets as the lowest excited states, their optical transitions do involve a change in spin state of 1 and thereby can harvest the triplet excitons in OLED devices.

Certain inefficient or non-emissive organometallic compounds satisfy the criteria of large spin-orbit coupling from the heavy metal and a charge transfer state as the lowest excited state. However, the charge transfer states are dominated by nonradiative processes (T. J. Meyer et al, *Inorg. Chem.*, 34, 473 (1995)). These processes are influenced by the vibrational overlap between the initial and final states in the acceptor modes (E. M. Kober et al *J. Phys. Chem.*, 90, 3722, (1986)). The rate constant for nonradiative decay increases as the vibrational overlap increases (T. J. Meyer et al, *Inorg. Chem.*, 34, 473 (1995)). One strategy to reduce the rate constant of nonradiative decay is through the π-delocalizaton of the acceptor ligand in the excited state.

Arene-transition metal complexes are known to be particularly stable organometallic compounds and represent a class of organometallics compounds that provide a heavy metal with a large spin-orbit coupling constant and a metal to ligand charge transfer state as the lowest excited states (J. A. Crayston et al., *J. Organomet. Chem.*, 423, 237, (1992)). However, these materials are not known as phosphorescent compounds apparently due to the dominant nonradiative decay processes.

There remains a need for new organometallic materials that will function as phosphorescent materials having improved efficiency, stability, manufacturability, or spectral characteristics.

SUMMARY OF THE INVENTION

The invention provides an electroluminescent device comprising a light-emitting layer containing a light emitting phosphorescent material that contains an organometallic complex comprising a metal selected from the group consisting of Mo, W, Re, Ru, and Os that is coordinated to a neutral or negatively-charged ligand group through the π electrons of the ligand with a hapticity greater than 2. The invention also provides a display or area lighting device including the OLED device, a process for emitting light, and an organometallic complex.

The device provides useful light emissions.

BRIEF DESCRIPTION OF THE DRAWINGS

FIG. 2 shows analytical data in support of Synthetic Example 1.

DETAILED DESCRIPTION OF THE INVENTION

Figure 1:
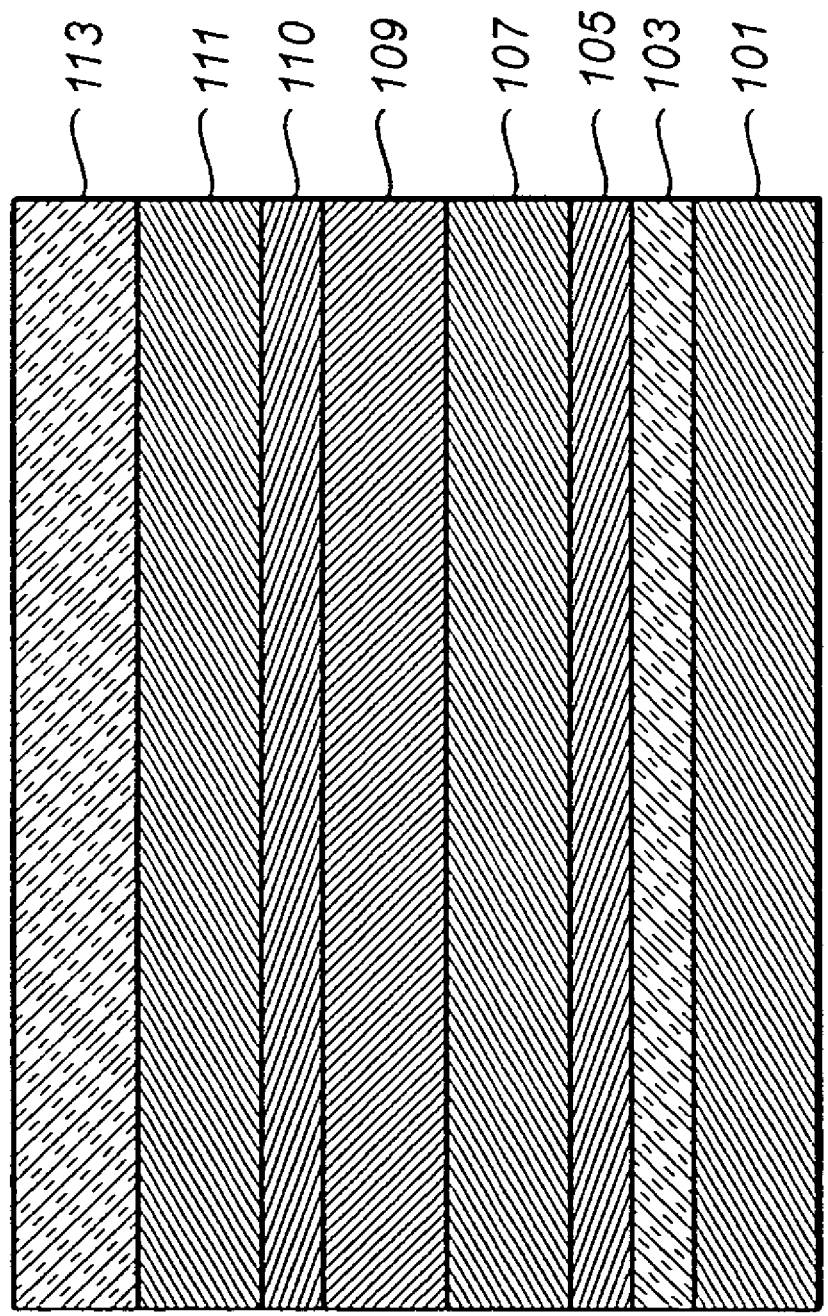
FIG. 1 shows a schematic cross-section of a typical OLED device in which this invention may be used.

The invention is summarized above. The arene or π bonding ligand has a substituent with a triplet excited state higher in energy than the π bonded-transition metal moiety. It is desirable that the substituent also provides delocalization through a conjugated π system to lower the rate constant of nonradiative decay processes.

These organometallic complexes provide the first examples of phosphorescent arene-transition metal complexes.

It is important that the hapticity of the ligand be greater than 2. Hapticity is defined as the number of atoms in the ligand within bonding distance to the metal center. It is further desirable that the π bonding ligand be aromatic forming an arene-transition metal bond. An arene-transition metal bond is defined as a bond formed between the π density of an aromatic ring and the transition metal center. Bonding occurs formally through each atom of the coordinated aromatic ring with the transition metal center.

In one useful embodiment of the invention, the π electron density of a neutral aromatic ring is comprised of six electrons and is coordinated to a Group VI or Group VII transition metal. For another useful embodiment, a negatively charged aromatic ring comprised of six π electrons is coordinated to Group VII and Group VIIII A transition metals. Examples of π bonding ligands are shown below, where R is any non-hydrogen substituent.

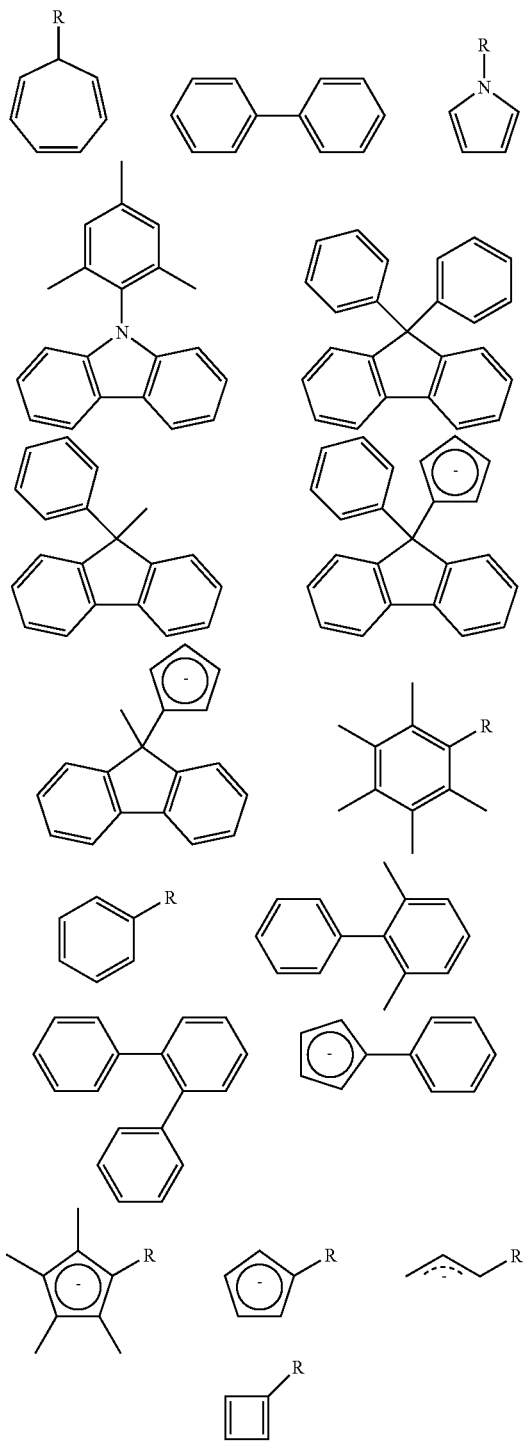

In one desirable embodiment, the ligand complexed to the metal is substituted with a group that provides π-delocalization through a conjugated system. It is desirable that the ligand be chosen so that the phosphorescence of the complex is visible to the eye, and it is further desirable for highly phosphorescent materials that the triplet state not be a π to π* ligand state.

The character of the triplet state may be determined through density functional theory calculations. A preferred method uses the B3LYP method as implemented in the Jaguar 4.1 computer code (Schrodinger, Inc., Portland Oreg.) with standard literature basis sets and pseudopotentials. A complex with the proper triplet state will comprise significant metal character in the highest-energy occupied molecular orbital or the lowest-energy unoccupied molecular orbital of the optimized ground state.

In one desirable embodiment, the organometallic complex can be represented by Formula (1).

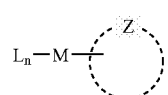

(1)

In Formula (1), M represents a coordinated metal selected from the group consisting of Mo, W, Re, Ru, and Os. In one suitable embodiment, M represents W, Re or Os, and more desirably M represents W.

Z represents the atoms necessary to form a ligand group that is neutral or negatively charged and that donates π electron density to M with hapticity greater than 2.

L represents independently selected ligand groups. The ligand or ligands are chosen so that they can complex to the metal and create a neutral complex with 18 electrons in the valence shell of M. For example, L can represent cyanide, halogen, carbon monoxide, benzene, $\eta^6$-benzene, $\eta^5$-cyclopentadienyl anion (Cp), or $\eta^5$-pentamethylcyclopentadienyl anion (Cp*), but is not limited to these ligands or their substituted forms. When M represents W, L is preferably carbon monoxide.

In Formula (1), n is 1-4, as necessary to fulfill the requirements of a neutral complex with 18 electrons in the valence shell of M. For example, when M represents W and L represents carbon monoxide, then n is 3.

In one suitable embodiment, Z represents a 5- or 6-membered aromatic ring, such as a phenyl group.

In another suitable embodiment, Z can be represented by Formula (2).

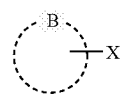

(2)

In Formula (2), B represents the atoms necessary to form a 5- or 6-membered aromatic ring group.

X represents a substituent group that provides π-delocalization through a conjugated system. The π system of X may be conjugated to the π system of B, it may be isolated from the π system of B by one or more saturated carbons, or it may be rotated orthogonally to the π system of B so that there is minimal π overlap between the two systems. In a suitable embodiment, X is chosen so that the phosphorescence of the complex is visible to the eye, and it is further desirable that the triplet state not be a π to π* ligand state. In one useful embodiment, X in Formula (2) comprises a fluorene group.

In one desirable embodiment of Formula (1), M represents W, L represents carbon monoxide, n is 3, and Z represents 9-diphenylfluorene.

In one useful embodiment of Formula (1), M represents Re, Os or Ru, and Z comprises a Cp or Cp* group.

Examples of the preparation of arene-transition metal complexes with a six-membered and five-membered aromatic ring respectively are provided in the following literature references; V. Desobry et al., *Helv. Chim.*, 64, 1288 (1981) and S. Dev et al., *J. Organomet. Chem.*, 469, 107 (1994).

Illustrative examples of complexes of Formula (1) useful in the present invention are the following:

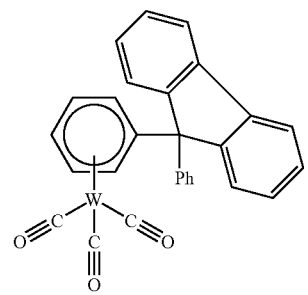

Inv-1

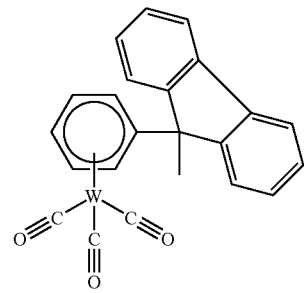

Inv-2

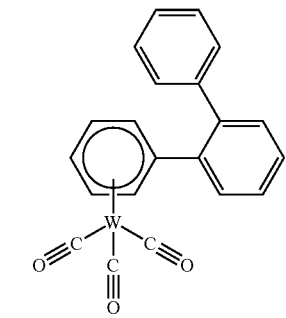

Inv-3

-continued
Inv-4
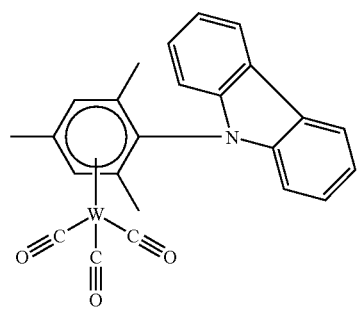
Inv-5
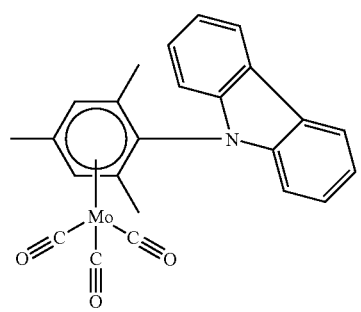
Inv-6
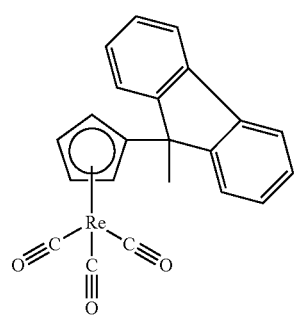
Inv-7
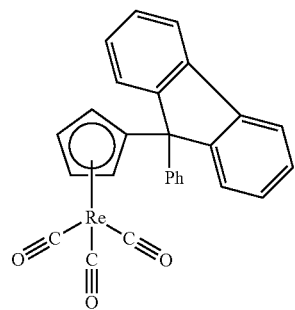
-continued
Inv-8
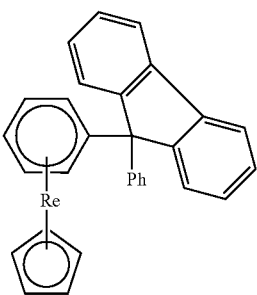
Inv-9
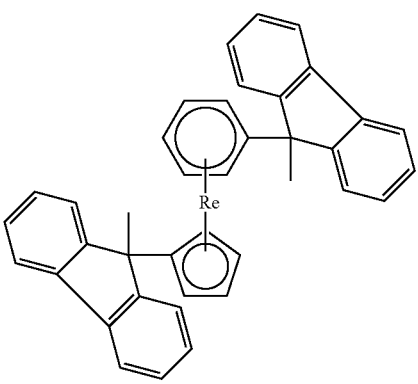
Inv-10
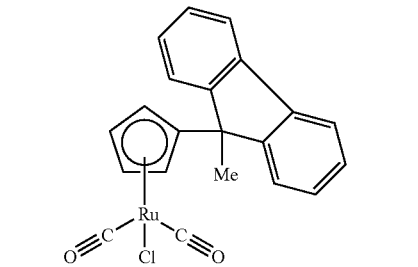
Inv-11
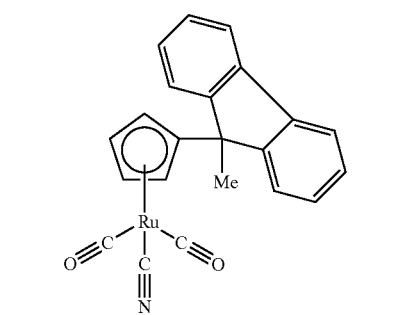

-continued
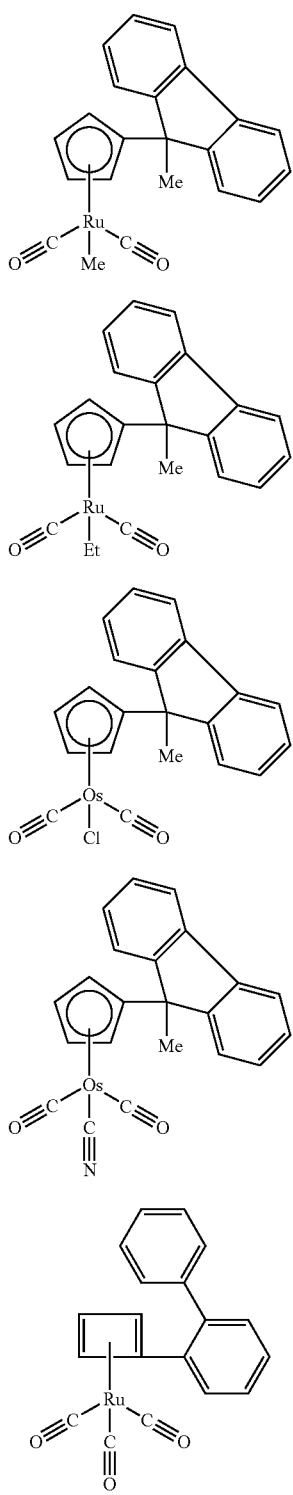
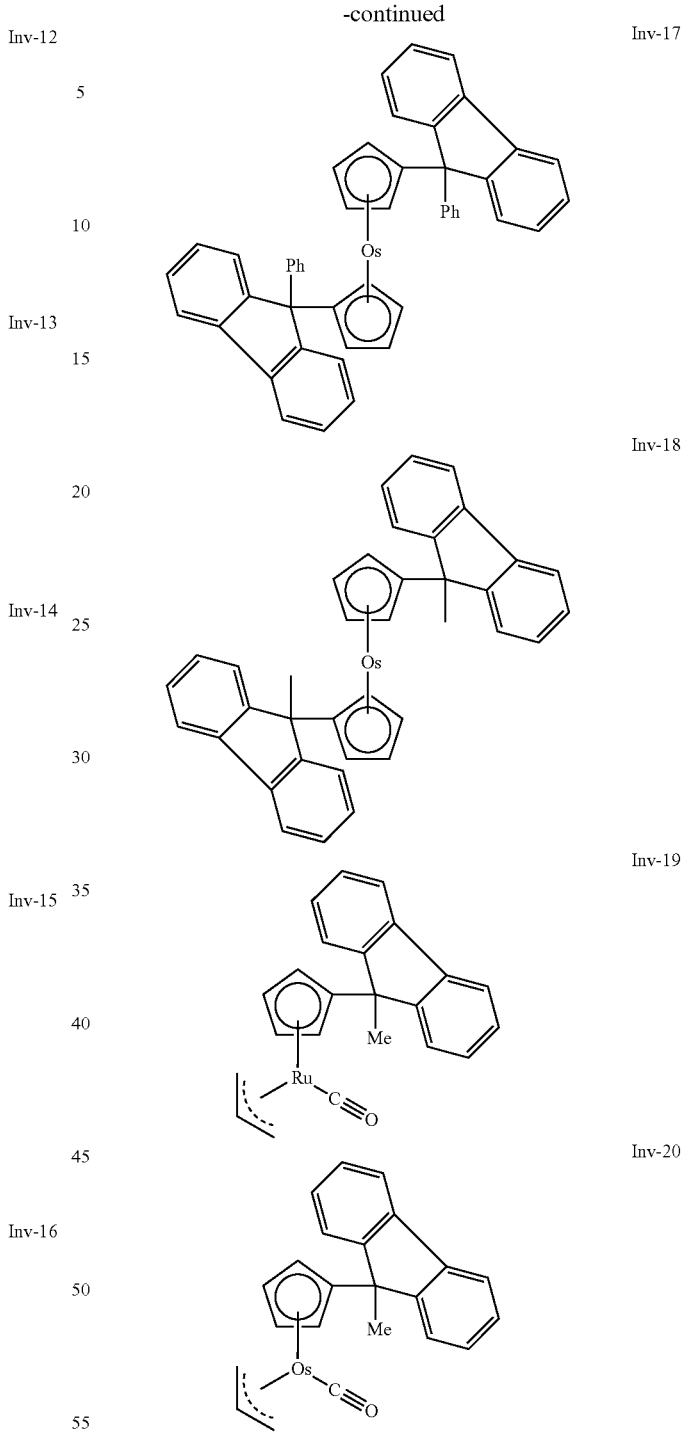
A desirable embodiment is represented by the general metallocene formulas 4A, 4B, and 4C shown below where M=Os, Ru, Re or W. In each structure, $R_1$, $R_2$, $R_3$, $R_4$, $R_5$ or $R_6$ represent hydrogen or a substituent where at least one $R_1$, $R_2$, $R_3$, $R_4$, $R_5$ or $R_6$ represents a substituent group that is conjugated with the coordinating aromatic ring. There can be multiple substituents conjugated to one or two coordinating rings. The conjugated substituents can be aromatic or aliphatic with aromatic groups being more desirable. The embodiment may also include non-conjugated substituents that are electron donating or electron withdrawing with electron donating groups typically being more desirable.

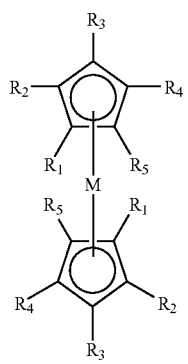

4A

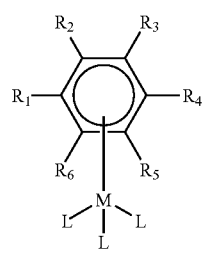

4B

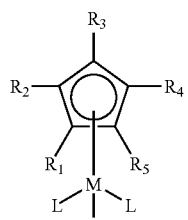

4C

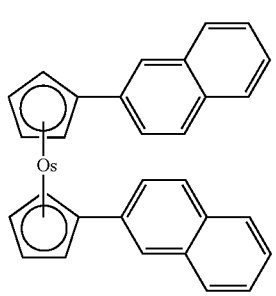

Inv-21

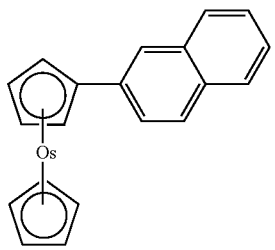

Inv-22

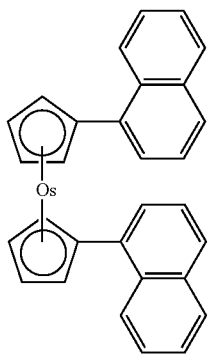

Inv-23

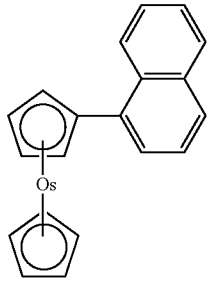

Inv-24

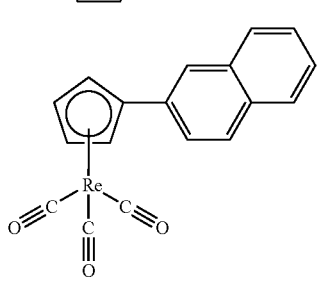

Inv-25

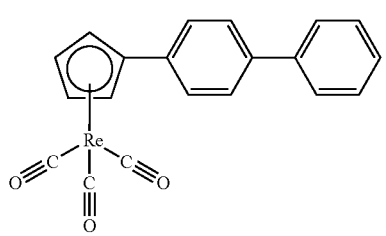

Inv-26

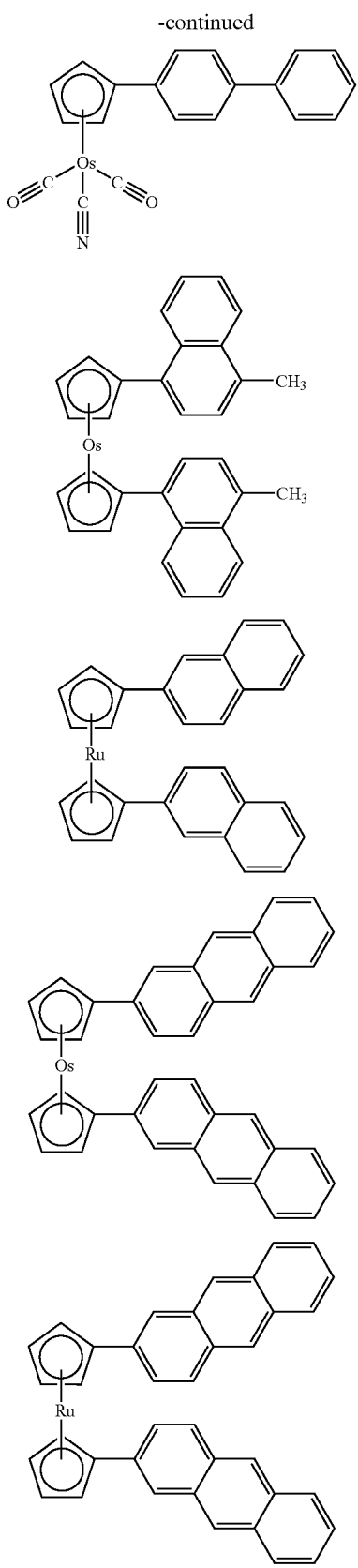

-continued

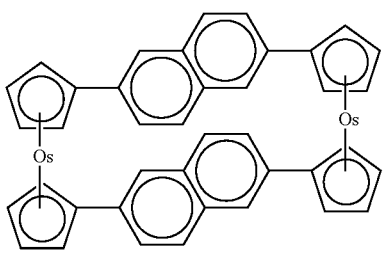

Inv-37

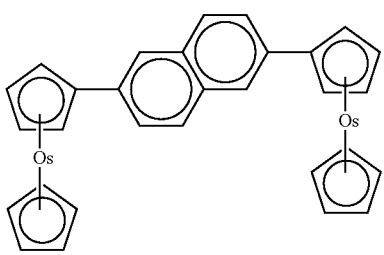

Inv-38

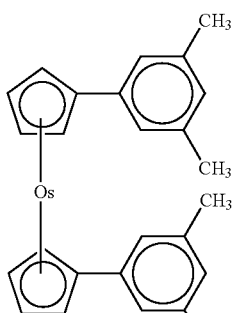

Inv-39

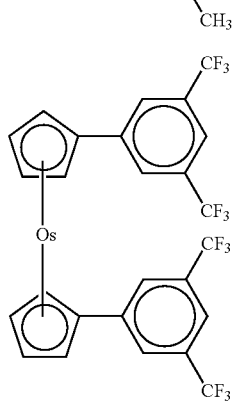

Inv-40

The compounds of formula (3) are believed to be novel:

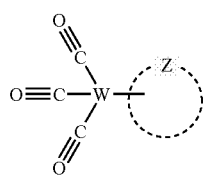

(3)

wherein Z is chosen from the group consisting of 9,9-diphenylfluorene, 9-phenyl-9-alkylfluorene, and o-terphenyl groups. These compounds are prepared as outlined in the examples.

Unless otherwise specifically stated, use of the term "substituted" or "substituent" means any group or atom other than hydrogen. Unless otherwise provided, when a group (including a compound or complex) containing a substitutable hydrogen is referred to, it is also intended to encompass not only the unsubstituted form, but also form further substituted derivatives with any substituent group or groups as herein mentioned, so long as the substituent does not destroy properties necessary for utility. Suitably, a substituent group may be halogen or may be bonded to the remainder of the molecule by an atom of carbon, silicon, oxygen, nitrogen, phosphorous, sulfur, selenium, or boron. The substituent may be, for example, halogen, such as chloro, bromo or fluoro; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy)butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl)carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonanido, benzenesulfonamido, p-tolylsulfonamido, p-dodecylbenzenesulfonamido, N-methyltetradecylsulfonamido, N,N-dipropyl-sulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl, N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such as methoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1 (N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen, sulfur, phosphorous, or boron. such as 2-furyl, 2-thienyl, 2-benzimidazolyloxy or 2-benzothiazolyl; quaternary ammonium, such as triethylammonium; quaternary phosphonium, such as triphenylphosphonium; and silyloxy, such as trimethylsilyloxy.

If desired, the substituents may themselves be further substituted one or more times with the described substituent groups. The particular substituents used may be selected by those skilled in the art to attain the desired desirable properties for a specific application and can include, for example, electron-withdrawing groups, electron-donating groups, and steric groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

Suitably, the light-emitting layer of the OLED device comprises a host material and one or more guest materials for emitting light. At least one of the guest materials is suitably a phosphorescent complex comprising Formula 1. The light-emitting guest material(s) is usually present in an amount less than the amount of host materials and is typically present in an amount of up to 20 wt % of the host, more typically from 2.0-10.0 wt % of the host For convenience, the phosphorescent complex guest material may be referred to herein as a phosphorescent material. The phosphorescent material of Formula 1 is preferably a low molecular weight compound, but it may also be an oligomer or a polymer having a main chain or a side chain of repeating units having the moiety represented by Formula 1. It may be provided as a discrete material dispersed in the host material, or it may be bonded in some way to the host material, for example, covalently bonded into a polymeric host.

Host Materials for Phosphorescent Materials

Suitable host materials should be selected so that the triplet exciton can be transferred efficiently from the host material to the phosphorescent material. For this transfer to occur, it is a highly desirable condition that the excited state energy of the phosphorescent material be lower than the difference in energy between the lowest triplet state and the ground state of the host. However, the band gap of the host should not be chosen so large as to cause an unacceptable increase in the drive voltage of the OLED. Suitable host materials are described in WO 00/70655 A2; 01/39234 A2; 01/93642 A1; 02/074015 A2; 02/15645 A1, and US 20020117662. Suitable hosts include certain aryl amines, triazoles, indoles and carbazole compounds. Examples of desirable hosts are 4,4'-N, N'-dicarbazole-biphenyl (CBP), 2,2'-dimethyl-4,4'-N,N'-dicarbazole-biphenyl, m-(N,N'-dicarbazole)benzene, and poly (N-vinylcarbazole), including their derivatives.

Desirable host materials are capable of forming a continuous film. The light-emitting layer may contain more than one host material in order to improve the device's film morphology, electrical properties, light emission efficiency, and lifetime. The light emitting layer may contain a first host material that has good hole-transporting properties, and a second host material that has good electron-transporting properties.

Other Phosphorescent Materials

Phosphorescent materials of Formula 1 may be used in combination with other phosphorescent materials, either in the same or different layers. Some other phosphorescent materials are described in WO 00/57676, WO 00/70655, WO 01/41512 A1, WO 02/15645 A1, US 2003/0017361 A1, WO 01/93642 A1, WO 01/39234 A2, U.S. Pat. No. 6,458,475 B1, WO 02/071813 A1, U.S. Pat. No. 6,573,651 B2, US 2002/0197511 A1, WO 02/074015 A2, U.S. Pat. No. 6,451,455 B1, US 2003/ 0072964 A1, US 2003 / 0068528 A1, U.S. Pat. No. 6,413,656 B1, U.S. Pat. No. 6,515,298 B2, U.S. Pat. No. 6,451,415 B1, U.S. Pat. No. 6,097,147, US 2003/0124381 A1, US 2003/0059646 A1, US 2003/0054198 A1, EP 1 239 526 A2, EP 1 238 981 A2, EP 1 244 155 A2, US 2002/0100906 A1, US 2003 / 0068526 A1, US 2003/0068535 A1, JP 2003073387A, JP 2003 073388A, US 2003/0141809 A1, US 2003/0040627 A1, JP 2003059667A, JP 2003073665A, and US 2002/0121638 A1.

The emission wavelengths of cyclometallated Ir(III) complexes of the type $IrL_3$ and $IrL_2L'$, such as the green-emitting fac-tris(2-phenylpyridinato-N,$C^{2'}$)iridium(III) and bis(2-phenylpyridinato-N,$C^{2'}$)iridium(III)(acetylacetonate) may be shifted by substitution of electron donating or withdrawing groups at appropriate positions on the cyclometallating ligand L, or by choice of different heterocycles for the cyclometallating ligand L. The emission wavelengths may also be shifted by choice of the ancillary ligand L'. Examples of red emitters are the bis(2-(2'-benzothienyl)pyridinato-N,$C^{3'}$)iridium(II)(acetylacetonate) and tris(1-phenylisoquinolinato-N,C)iridium(III). A blue-emitting example is bis(2-(4,6-diflourophenyl)-pyridinato-N,$C^{2'}$)iridium(III)(picolinate).

Red electrophosphorescence has been reported, using bis (2-(2'-benzo[4,5-a]thienyl)pyridinato-N,$C^3$) iridium (acetylacetonate) [$Btp_2Ir(acac)$] as the phosphorescent material (Adachi, C., Lamansky, S., Baldo, M. A., Kwong, R. C., Thompson, M. E., and Forrest, S. R., *App. Phys. Lett.*, 78, 1622-1624 (2001).

Other important phosphorescent materials include cyclometallated Pt(II) complexes such as cis-bis(2-phenylpyridinato-N,$C^{2'}$)platinum(II), cis-bis(2-(2'-thienyl)pyridinato-N, $C^{3'}$) platinum(II), cis-bis(2-(2'-thienyl)quinolinato-N,$C^{5'}$) platinum(II), or (2-(4,6-diflourophenyl)pyridinato-NC2') platinum (II) acetylacetonate. Pt(II) porphyrin complexes such as 2,3,7,8,12,13,17,18-octaethyl-21H, 23H-porphine platinum(II) are also useful phosphorescent materials.

Still other examples of useful phosphorescent materials include coordination complexes of the trivalent lanthanides such as $Tb^{3+}$ and $Eu^{3+}$ (J. Kido et al, *Appl. Phys. Lett.*, 65, 2124 (1994)).

Blocking Layers

In addition to suitable hosts, an OLED device employing a phosphorescent material often requires at least one exciton- or hole- or electron-blocking layers to help confine the excitons or electron-hole recombination centers to the light-emitting layer comprising the host and phosphorescent material. In one embodiment, such a blocking layer would be placed between the electron-transporting layer and the light-emitting layer—see FIG. 1, layer 110. In this case, the ionization potential of the blocking layer should be such that there is an energy barrier for hole migration from the host into the electron-transporting layer, while the electron affinity should be such that electrons pass more readily from the electron-transporting layer into the light-emitting layer comprising host and phosphorescent material. It is further desired, but not absolutely required, that the triplet energy of the blocking material be greater than that of the phosphorescent material. Suitable hole-blocking materials are described in WO 00/70655A2 and WO 01/93642 A1. Two examples of useful materials are bathocuproine (BCP) and bis(2-methyl-8-quinolinolato)(4-phenylphenolato)Aluminum(III) (BAlQ). Metal complexes other than Balq are also known to block holes and excitons as described in US 20030068528. US 20030175553 A1 describes the use of fac-tris(1-phenylpyrazolato-N,C2)iridium(III) (Irppz) in an electron/exciton blocking layer.

Embodiments of the invention can provide advantageous features such as operating efficiency, higher luminance, color hue, low drive voltage, and improved operating stability. Embodiments of the organometallic compounds useful in the invention can provide a wide range of hues including those useful in the emission of white light (directly or through filters to provide multicolor displays).

General Device Architecture

The present invention can be employed in many OLED device configurations using small molecule materials, oligomeric materials, polymeric materials, or combinations thereof. These include very simple structures comprising a single anode and cathode to more complex devices, such as passive matrix displays comprised of orthogonal arrays of anodes and cathodes to form pixels, and active-matrix displays where each pixel is controlled independently, for example, with thin film transistors (TFTs).

There are numerous configurations of the organic layers wherein the present invention can be successfully practiced. The essential requirements of an OLED are an anode, a cathode, and an organic light-emitting layer located between the anode and cathode. Additional layers may be employed as more fully described hereafter.

A typical structure, especially useful for of a small molecule device, is shown in FIG. 1 and is comprised of a substrate 101, an anode 103, a hole-injecting layer 105, a hole-transporting layer 107, a light-emitting layer 109, a hole- or exciton-blocking layer 110, an electron-transporting layer 111, and a cathode 113. These layers are described in detail below. Note that the substrate may alternatively be located adjacent to the cathode, or the substrate may actually constitute the anode or cathode. The organic layers between the anode and cathode are conveniently referred to as the organic EL element. Also, the total combined thickness of the organic layers is desirably less than 500 nm.

The anode and cathode of the OLED are connected to a voltage/current source through electrical conductors. The OLED is operated by applying a potential between the anode and cathode such that the anode is at a more positive potential than the cathode. Holes are injected into the organic EL element from the anode and electrons are injected into the organic EL element at the cathode. Enhanced device stability can sometimes be achieved when the OLED is operated in an AC mode where, for some time period in the cycle, the potential bias is reversed and no current flows. An example of an AC driven OLED is described in U.S. Pat. No. 5,552,678.

Substrate

The OLED device of this invention is typically provided over a supporting substrate 101 where either the cathode or anode can be in contact with the substrate. The electrode in contact with the substrate is conveniently referred to as the bottom electrode. Conventionally, the bottom electrode is the anode, but this invention is not limited to that configuration. The substrate can either be light transmissive or opaque, depending on the intended direction of light emission. The light transmissive property is desirable for viewing the EL emission through the substrate. Transparent glass or plastic is commonly employed in such cases. The substrate can be a complex structure comprising multiple layers of materials. This is typically the case for active matrix substrates wherein TFTs are provided below the OLED layers. It is still necessary that the substrate, at least in the emissive pixilated areas, be comprised of largely transparent materials such as glass or polymers. For applications where the EL emission is viewed through the top electrode, the transmissive characteristic of the bottom support is immaterial, and therefore can be light transmissive, light absorbing or light reflective. Substrates for use in this case include, but are not limited to, glass, plastic, semiconductor materials, silicon, ceramics, and circuit board materials. Again, the substrate can be a complex structure comprising multiple layers of materials such as found in active matrix TFT designs. It is necessary to provide in these device configurations a light-transparent top electrode.

Anode

When the desired electroluminescent light emission (EL) is viewed through the anode, the anode should be transparent or substantially transparent to the emission of interest. Common transparent anode materials used in this invention are indium-tin oxide (ITO), indium-zinc oxide (IZO) and tin oxide, but other metal oxides can work including, but not limited to, aluminum- or indium-doped zinc oxide, magnesium-indium oxide, and nickel-tungsten oxide. In addition to these oxides, metal nitrides, such as gallium nitride, and metal selenides, such as zinc selenide, and metal sulfides, such as zinc sulfide, can be used as the anode. For applications where EL emission is viewed only through the cathode, the transmissive characteristics of the anode are immaterial and any conductive material can be used, transparent, opaque or reflective. Example conductors for this application include, but are not limited to, gold, iridium, molybdenum, palladium, and platinum. Typical anode materials, transmissive or otherwise, have a work function of 4.1 eV or greater. Desired anode materials are commonly deposited by any suitable means such as evaporation, sputtering, chemical vapor deposition, or electrochemical means. Anodes can be patterned using well-known photolithographic processes. Optionally, anodes may be polished prior to application of other layers to reduce surface roughness so as to minimize shorts or enhance reflectivity.

Cathode

When light emission is viewed solely through the anode, the cathode used in this invention can be comprised of nearly any conductive material. Desirable materials have good film-forming properties to ensure good contact with the underlying organic layer, promote electron injection at low voltage, and have good stability. Useful cathode materials often contain a low work function metal (<4.0 eV) or metal alloy. One useful cathode material is comprised of a Mg:Ag alloy wherein the percentage of silver is in the range of 1 to 20%, as described in U.S. Pat. No. 4,885,221. Another suitable class of cathode materials includes bilayers comprising the cathode and a thin electron-injection layer (EIL) in contact with an organic layer (e.g., an electron transporting layer (ETL)) which is capped with a thicker layer of a conductive metal. Here, the EIL preferably includes a low work function metal or metal salt, and if so, the thicker capping layer does not need to have a low work function. One such cathode is comprised of a thin layer of LiF followed by a thicker layer of Al as described in U.S. Pat. No. 5,677,572. An ETL material doped with an alkali metal, for example, Li-doped Alq, is another example of a useful EIL. Other useful cathode material sets include, but are not limited to, those disclosed in U.S. Pat. Nos. 5,059,861, 5,059,862, and 6,140,763.

When light emission is viewed through the cathode, the cathode must be transparent or nearly transparent. For such applications, metals must be thin or one must use transparent conductive oxides, or a combination of these materials. Optically transparent cathodes have been described in more detail in U.S. Pat. Nos. 4,885,211, 5,247,190, JP 3,234,963, U.S. Pat. Nos. 5,703,436, 5,608,287, 5,837,391, 5,677,572, 5,776,622, 5,776,623, 5,714,838, 5,969,474, 5,739,545, 5,981,306, 6,137,223, 6,140,763, 6,172,459, EP 1 076 368, U.S. Pat. Nos. 6,278,236, and 6,284,393. Cathode materials are typically deposited by any suitable method such as evaporation, sputtering, or chemical vapor deposition. When needed, patterning can be achieved through many well known methods including, but not limited to, through-mask deposition, integral shadow masking as described in U.S. Pat. No. 5,276,380 and EP 0 732 868, laser ablation, and selective chemical vapor deposition.

Hole-Injecting Layer (HIL)

A hole-injecting layer 105 may be provided between anode 103 and hole-transporting layer 107. The hole-injecting material can serve to improve the film formation property of subsequent organic layers and to facilitate injection of holes into the hole-transporting layer. Suitable materials for use in the hole-injecting layer include, but are not limited to, porphyrinic compounds as described in U.S. Pat. No. 4,720,432, plasma-deposited fluorocarbon polymers as described in U.S. Pat. No. 6,208,075, and some aromatic amines, for example, m-MTDATA (4,4',4"-tris[(3-methylphenyl)phenylamino]triphenylamine). Alternative hole-injecting materials reportedly useful in organic EL devices are described in EP 0 891 121 A1 and EP 1 029 909 A1.

Hole-Transporting Layer (HTL)

The hole-transporting layer 107 of the organic EL device contains at least one hole-transporting compound such as an aromatic tertiary amine, where the latter is understood to be a compound containing at least one trivalent nitrogen atom that is bonded only to carbon atoms, at least one of which is a member of an aromatic ring. In one form the aromatic tertiary amine can be an arylamine, such as a monoarylamine, diarylamine, triarylamine, or a polymeric arylamine. Exemplary monomeric triarylamines are illustrated by Klupfel et al. U.S. Pat. No. 3,180,730. Other suitable triarylamines substituted with one or more vinyl radicals and/or comprising at least one active hydrogen containing group are disclosed by Brantley et al U.S. Pat. Nos. 3,567,450 and 3,658,520.

A more preferred class of aromatic tertiary amines are those which include at least two aromatic tertiary amine moieties as described in U.S. Pat. Nos. 4,720,432 and 5,061,569. Such compounds include those represented by structural formula (A).

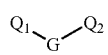

A wherein $Q_1$ and $Q_2$ are independently selected aromatic tertiary amine moieties and G is a linking group such as an arylene, cycloalkylene, or alkylene group of a carbon to carbon bond. In one embodiment, at least one of $Q_1$ or $Q_2$ contains a polycyclic fused ring structure, e.g., a naphthalene. When G is an aryl group, it is conveniently a phenylene, biphenylene, or naphthalene moiety.

A useful class of triarylamines satisfying structural formula (A) and containing two triarylamine moieties is represented by structural formula (B):

B where
  $R_1$ and $R_2$ each independently represents a hydrogen atom, an aryl group, or an alkyl group or $R_1$ and $R_2$ together represent the atoms completing a cycloalkyl group; and
  $R_3$ and $R_4$ each independently represents an aryl group, which is in turn substituted with a diaryl substituted amino group, as indicated by structural formula (C):

C wherein $R_5$ and $R_6$ are independently selected aryl groups. In one embodiment, at least one of $R_5$ or $R_6$ contains a polycyclic fused ring structure, e.g., a naphthalene.

Another class of aromatic tertiary amines are the tetraaryldiamines. Desirable tetraaryldiamines include two diarylamino groups, such as indicated by formula (C), linked through an arylene group. Useful tetraaryldiamines include those represented by formula (D).

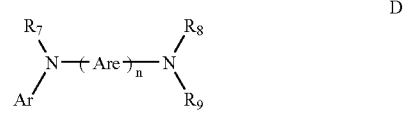

D wherein
  each Are is an independently selected arylene group, such as a phenylene or anthracene moiety,
  n is an integer of from 1 to 4, and
  Ar, $R_7$, $R_8$, and $R_9$ are independently selected aryl groups.

In a typical embodiment, at least one of Ar, $R_7$, $R_8$, and $R_9$ is a polycyclic fused ring structure, e.g., a naphthalene.

The various alkyl, alkylene, aryl, and arylene moieties of the foregoing structural formulae (A), (B), (C), (D), can each in turn be substituted. Typical substituents include alkyl groups, alkoxy groups, aryl groups, aryloxy groups, and halogen such as fluoride, chloride, and bromide. The various alkyl and alkylene moieties typically contain from about 1 to 6 carbon atoms. The cycloalkyl moieties can contain from 3 to about 10 carbon atoms, but typically contain five, six, or seven ring carbon atoms—e.g., cyclopentyl, cyclohexyl, and cycloheptyl ring structures. The aryl and arylene moieties are usually phenyl and phenylene moieties.

The hole-transporting layer can be formed of a single or a mixture of aromatic tertiary amine compounds. Specifically, one may employ a triarylamine, such as a triarylamine satisfying the formula (B), in combination with a tetraaryldiamine, such as indicated by formula (D). When a triarylamine is employed in combination with a tetraaryldiamine, the latter is positioned as a layer interposed between the triarylamine and the electron injecting and transporting layer. Illustrative of useful aromatic tertiary amines are the following:

1,1-Bis(4-di-p-tolylaminophenyl)cyclohexane
1,1-Bis(4-di-p-tolylaminophenyl)-4-phenylcyclohexane
N,N,N',N'-tetraphenyl-4,4'''-diamino-1,1':4', 1":4"', 1'''-quaterphenyl
Bis(4-dimethylamino-2-methylphenyl)phenylmethane
1,4-bis[2-[4-[N,N-di(p-toly)amino]phenyl]vinyl]benzene (BDTAPVB)
N,N,N',N'-Tetra-p-tolyl-4,4'-diaminobiphenyl
N,N,N',N'-Tetraphenyl-4,4'-diaminobiphenyl
N,N,N',N'-tetra-1-naphthyl-4,4'-diaminobiphenyl
N,N,N',N'-tetra-2-naphthyl-4,4'-diaminobiphenyl
N-Phenylcarbazole
4,4'-Bis[N-(1-naphthyl)-N-phenylamino]biphenyl (NPB)
4,4'-Bis[N-(1-naphthyl)-N-(2-naphthyl)amino]biphenyl (TNB)
4,4'-Bis[N-(1-naphthyl)-N-phenylamino]p-terphenyl
4,4'-Bis[N-(2-naphthyl)-N-phenylamino]biphenyl
4,4'-Bis[N-(3-acenaphthenyl)-N-phenylamino]biphenyl
1,5-Bis[N-(1-naphthyl)-N-phenylamino]naphthalene
4,4'-Bis[N-(9-anthryl)-N-phenylamino]biphenyl
4,4'-Bis[N-(1-anthryl)-N-phenylamino]-ρ-terphenyl
4,4'-Bis[N-(2-phenanthryl)-N-phenylamino]biphenyl
4,4'-Bis[N-(8-fluoranthenyl)-N-phenylamino]biphenyl
4,4'-Bis[N-(2-pyrenyl)-N-phenylamino]biphenyl
4,4'-Bis[N-(2-naphthacenyl)-N-phenylamino]biphenyl
4,4'-Bis[N-(2-perylenyl)-N-phenylamino]biphenyl
4,4'-Bis[N-(1-coronenyl)-N-phenylamino]biphenyl
2,6-Bis(di-ρ-tolylamino)naphthalene
2,6-Bis[di-(1-naphthyl)amino]naphthalene
2,6-Bis[N-(1-naphthyl)-N-(2-naphthyl)amino]naphthalene
N,N,N',N'-Tetra(2-naphthyl)-4,4"-diamino-ρ-terphenyl
4,4'-Bis{N-phenyl-N-[4-(1-naphthyl)-phenyl]amino}biphenyl
2,6-Bis[N,N-di(2-naphthyl)amino]fluorene
4,4',4"-tris[(3-methylphenyl)phenylamino]triphenylamine (MTDATA)
4,4'-Bis[N-(3-methylphenyl)-N-phenylamino]biphenyl (TPD)

Another class of useful hole-transporting materials includes polycyclic aromatic compounds as described in EP 1 009 041. Tertiary aromatic amines with more than two amine groups may be used including oligomeric materials. In addition, polymeric hole-transporting materials can be used such as poly(N-vinylcarbazole)(PVK), polythiophenes, polypyrrole, polyaniline, and copolymers such as poly(3,4-ethylenedioxythiophene)/poly(4-styrenesulfonate) also called PEDOT/PSS.

Fluorescent Light-Emitting Materials and Layers (LEL)

In addition to the phosphorescent materials of this invention, other light emitting materials may be used in the OLED device, including fluorescent materials. Although the term "fluorescent" is commonly used to describe any light emitting material, in this case we are referring to a material that emits light from a singlet excited state. Fluorescent materials may be used in the same layer as the phosphorescent material, in adjacent layers, in adjacent pixels, or any combination. Care must be taken not to select materials that will adversely affect the performance of the phosphorescent materials of this invention. One skilled in the art will understand that triplet excited state energies of materials in the same layer as the phosphorescent material or in an adjacent layer must be appropriately set so as to prevent unwanted quenching.

As more fully described in U.S. Pat. Nos. 4,769,292 and 5,935,721, the light-emitting layer (LEL) of the organic EL element includes a luminescent fluorescent or phosphorescent material where electroluminescence is produced as a result of electron-hole pair recombination in this region. The light-emitting layer can be comprised of a single material, but more commonly consists of a host material doped with a guest emitting material or materials where light emission comes primarily from the emitting materials and can be of any color. The host materials in the light-emitting layer can be an electron-transporting material, as defined below, a hole-transporting material, as defined above, or another material or combination of materials that support hole-electron recombination. Fluorescent emitting materials are typically incorporated at 0.01 to 10% by weight of the host material.

The host and emitting materials can be small non-polymeric molecules or polymeric materials such as polyfluorenes and polyvinylarylenes (e.g., poly(p-phenylenevinylene), PPV). In the case of polymers, small molecule emitting materials can be molecularly dispersed into a polymeric host, or the emitting materials can be added by copolymerizing a minor constituent into a host polymer. Host materials may be mixed together in order to improve film formation, electrical properties, light emission efficiency, lifetime, or manufacturability. The host may comprise a material that has good hole-transporting properties and a material that has good electron-transporting properties.

An important relationship for choosing a fluorescent dye as a guest emitting material is a comparison of the singlet excited state energies of the host and light-emitting material. For efficient energy transfer from the host to the emitting material, a highly desirable condition is that the singlet excited state energy of the emitting material is lower than that of the host material.

Host and emitting materials known to be of use include, but are not limited to, those disclosed in U.S. Pat. Nos. 4,768,292, 5,141,671, 5,150,006, 5,151,629, 5,405,709, 5,484,922, 5,593,788, 5,645,948, 5,683,823, 5,755,999, 5,928,802, 5,935,720, 5,935,721, and 6,020,078.

Metal complexes of 8-hydroxyquinoline and similar derivatives (Formula E) constitute one class of useful host compounds capable of supporting electroluminescence, and are particularly suitable for light emission of wavelengths longer than 500 nm, e.g., green, yellow, orange, and red.

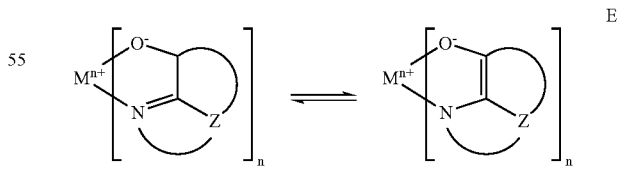

wherein
M represents a metal;
n is an integer of from 1 to 4; and
Z independently in each occurrence represents the atoms completing a nucleus having at least two fused aromatic rings.

From the foregoing it is apparent that the metal can be monovalent, divalent, trivalent, or tetravalent metal. The metal can, for example, be an alkali metal, such as lithium, sodium, or potassium; an alkaline earth metal, such as magnesium or calcium; an earth metal, such aluminum or gallium, or a transition metal such as zinc or zirconium. Generally any monovalent, divalent, trivalent, or tetravalent metal known to be a useful chelating metal can be employed.

Z completes a heterocyclic nucleus containing at least two fused aromatic rings, at least one of which is an azole or azine ring. Additional rings, including both aliphatic and aromatic rings, can be fused with the two required rings, if required. To avoid adding molecular bulk without improving on function the number of ring atoms is usually maintained at 18 or less.

Illustrative of useful chelated oxinoid compounds are the following:

CO-1: Aluminum trisoxine [alias, tris(8-quinolinolato)aluminum(III)]
CO-2: Magnesium bisoxine [alias, bis(8-quinolinolato)magnesium(II)]
CO-3: Bis[benzo{f}-8-quinolinolato]zinc(II)
CO-4: Bis(2-methyl-8-quinolinolato)aluminum(III)-μ-oxo-bis(2-methyl-8-quinolinolato)aluminum(III)
CO-5: Indium trisoxine [alias, tris(8-quinolinolato)indium]
CO-6: Aluminum tris(5-methyloxine) [alias, tris(5-methyl-8-quinolinolato)aluminum(III)]
CO-7: Lithium oxine [alias, (8-quinolinolato)lithium(I)]
CO-8: Gallium oxine [alias, tris(8-quinolinolato)gallium(III)]
CO-9: Zirconium oxine [alias, tetra(8-quinolinolato)zirconium(IV)]

Derivatives of 9,10-di-(2-naphthyl)anthracene (Formula F) constitute one class of useful host materials capable of supporting electroluminescence, and are particularly suitable for light emission of wavelengths longer than 400 nm, e.g., blue, green, yellow, orange or red.

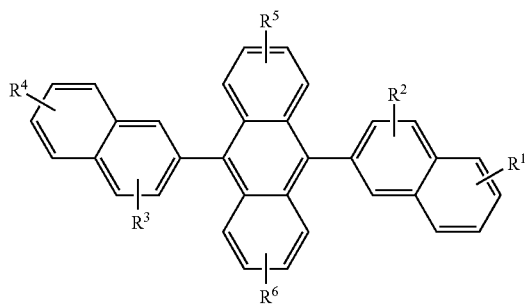

F wherein: $R^1$, $R^2$, $R^3$, $R^4$, $R^5$, and $R^6$ represent one or more substituents on each ring where each substituent is individually selected from the following groups:

Group 1: hydrogen, or alkyl of from 1 to 24 carbon atoms;
Group 2: aryl or substituted aryl of from 5 to 20 carbon atoms;
Group 3: carbon atoms from 4 to 24 necessary to complete a fused aromatic ring of anthracenyl; pyrenyl, or perylenyl;
Group 4: heteroaryl or substituted heteroaryl of from 5 to 24 carbon atoms as necessary to complete a fused heteroaromatic ring of furyl, thienyl, pyridyl, quinolinyl or other heterocyclic systems;
Group 5: alkoxylamino, alkylamino, or arylamino of from 1 to 24 carbon atoms; and
Group 6: fluorine, chlorine, bromine or cyano.

Illustrative examples include 9,10-di-(2-naphthyl)anthracene and 2-t-butyl-9,10-di-(2-naphthyl)anthracene. Other anthracene derivatives can be useful as a host in the LEL, including derivatives of 9,10-bis[4-(2,2-diphenylethenyl)phenyl]anthracene.

Benzazole derivatives (Formula G) constitute another class of useful host materials capable of supporting electroluminescence, and are particularly suitable for light emission of wavelengths longer than 400 nm, e.g., blue, green, yellow, orange or red.

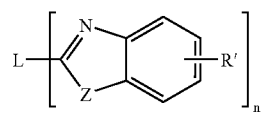

G

Where:
n is an integer of 3 to 8;
Z is O, NR or S; and
R and R' are individually hydrogen; alkyl of from 1 to 24 carbon atoms, for example, propyl, t-butyl, heptyl, and the like; aryl or hetero-atom substituted aryl of from 5 to 20 carbon atoms for example phenyl and naphthyl, furyl, thienyl, pyridyl, quinolinyl and other heterocyclic systems; or halo such as chloro, fluoro; or atoms necessary to complete a fused aromatic ring; and
L is a linkage unit consisting of alkyl, aryl, substituted alkyl, or substituted aryl, which conjugately or unconjugately connects the multiple benzazoles together. An example of a useful benzazole is 2, 2', 2"-(1,3,5-phenylene)tris[1-phenyl-1H-benzimidazole].

Styrylarylene derivatives as described in U.S. Pat. No. 5,121,029 and JP 08333569 are also useful hosts for blue emission. For example, 9,10-bis[4-(2,2-diphenylethenyl)phenyl]anthracene and 4,4'-Bis(2,2-diphenylethenyl)-1,1'-biphenyl (DPVBi) are useful hosts for blue emission.

Useful fluorescent emitting materials include, but are not limited to, derivatives of anthracene, tetracene, xanthene, perylene, rubrene, coumarin, rhodamine, and quinacridone, dicyanomethylenepyran compounds, thiopyran compounds, polymethine compounds, pyrilium and thiapyrilium compounds, fluorene derivatives, periflanthene derivatives, indenoperylene derivatives, bis(azinyl)amine boron compounds, bis(azinyl)methane compounds, and carbostyryl compounds. Illustrative examples of useful materials include, but are not limited to, the following:

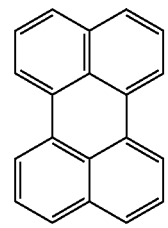

L1

-continued
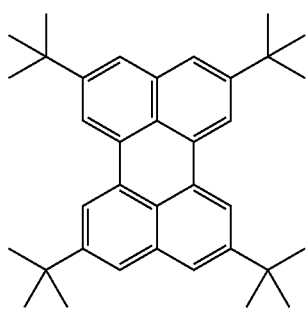
L2
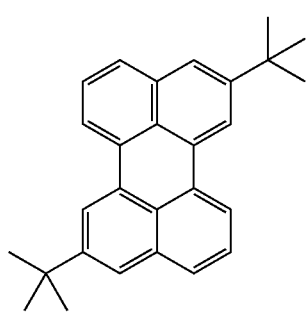
L3
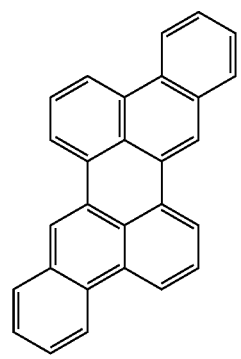
L4
-continued
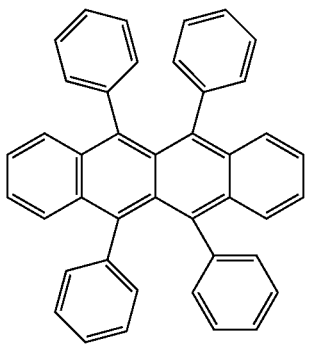
L5
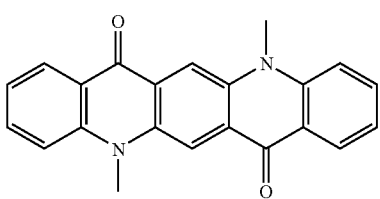
L6
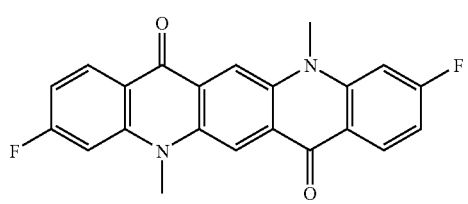
L7
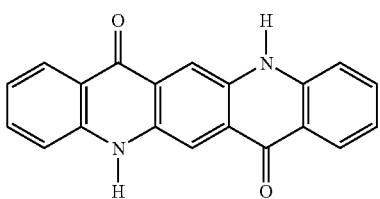
L8

-continued

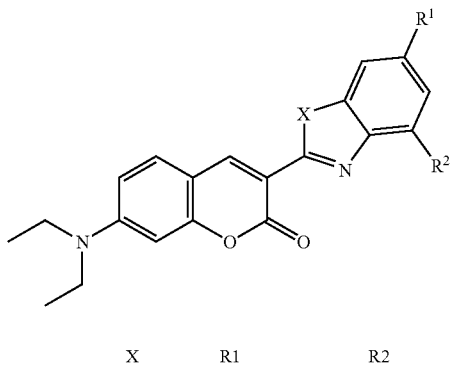

| | X | R1 | R2 |
|---|---|---|---|
| L9 | O | H | H |
| L10 | O | H | Methyl |
| L11 | O | Methyl | H |
| L12 | O | Methyl | Methyl |
| L13 | O | H | t-butyl |
| L14 | O | t-butyl | H |
| L15 | O | t-butyl | t-butyl |
| L16 | S | H | H |
| L17 | S | H | Methyl |
| L18 | S | Methyl | H |
| L19 | S | Methyl | Methyl |
| L20 | S | H | t-butyl |
| L21 | S | t-butyl | H |
| L22 | S | t-butyl | t-butyl |

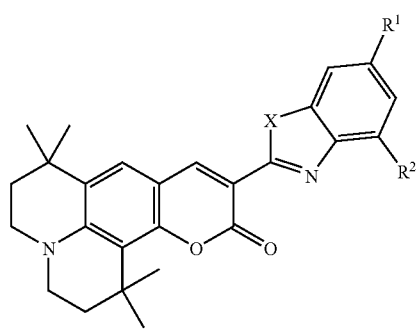

| | X | R1 | R2 |
|---|---|---|---|
| L23 | O | H | H |
| L24 | O | H | Methyl |
| L25 | O | Methyl | H |
| L26 | O | Methyl | Methyl |
| L27 | O | H | t-butyl |
| L28 | O | t-butyl | H |
| L29 | O | t-butyl | t-butyl |
| L30 | S | H | H |
| L31 | S | H | Methyl |
| L32 | S | Methyl | H |
| L33 | S | Methyl | Methyl |
| L34 | S | H | tbutyl |
| L35 | S | t-butyl | H |
| L36 | S | t-butyl | t-butyl |

-continued

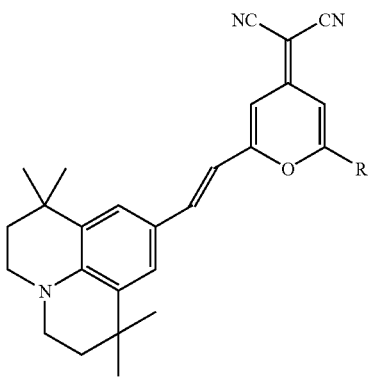

| | R |
|---|---|
| L37 | phenyl |
| L38 | methyl |
| L39 | t-butyl |
| L40 | mesityl |

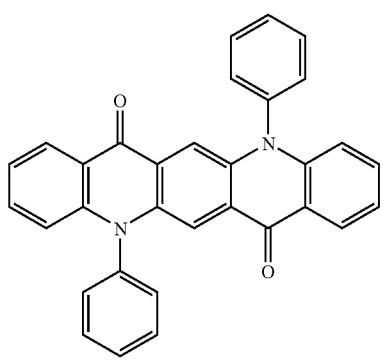

| | R |
|---|---|
| L41 | phenyl |
| L42 | methyl |
| L43 | t-butyl |
| L44 | mesityl |

L45

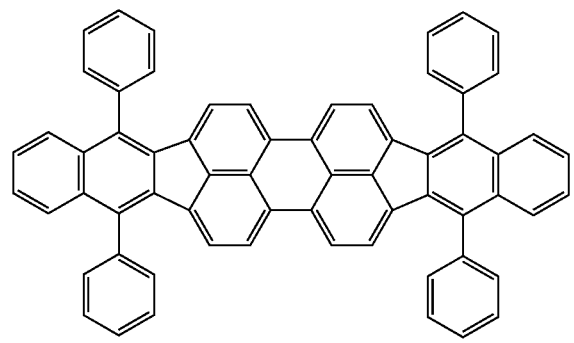
L46
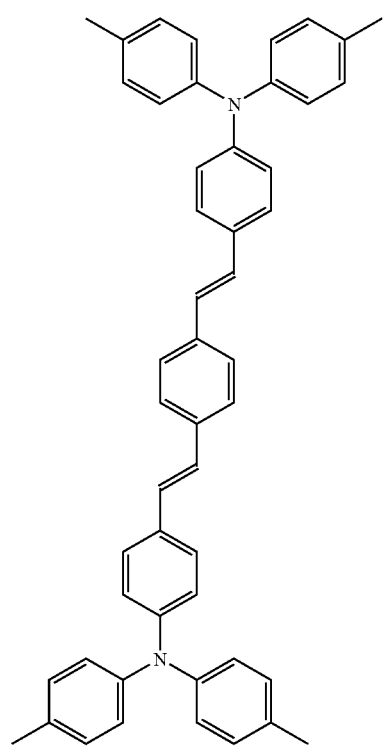
L47
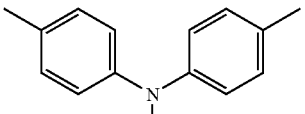
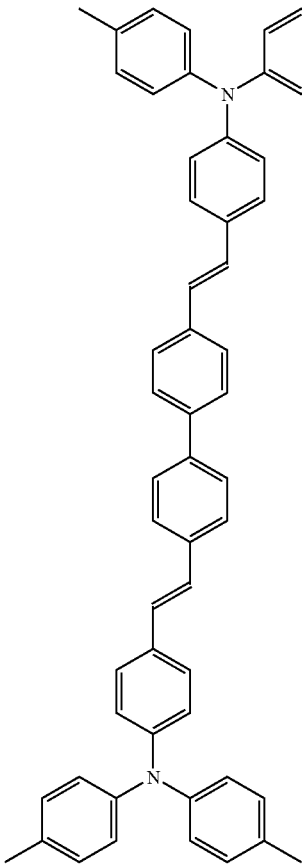
L48

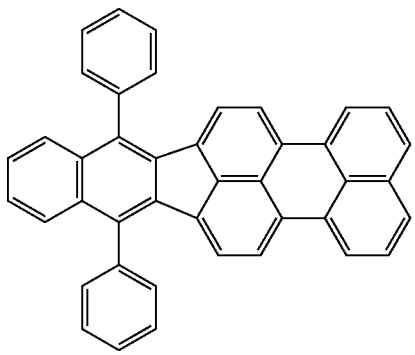

L49

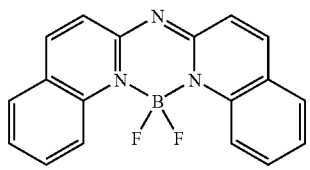

L50

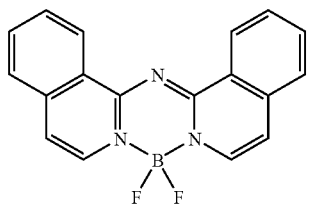

L51

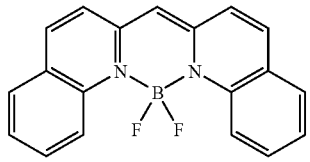

L52

Electron-Transporting Layer (ETL)

Preferred thin film-forming materials for use in forming the electron-transporting layer 111 of the organic EL devices of this invention are metal chelated oxinoid compounds, including chelates of oxine itself (also commonly referred to as 8-quinolinol or 8-hydroxyquinoline). Such compounds help to inject and transport electrons and exhibit both high levels of performance and are readily fabricated in the form of thin films. Exemplary of contemplated oxinoid compounds are those satisfying structural formula (E), previously described.

Other electron-transporting materials include various butadiene derivatives as disclosed in U.S. Pat. No. 4,356,429 and various heterocyclic optical brighteners as described in U.S. Pat. No. 4,539,507. Benzazoles satisfying structural formula (G) are also useful electron transporting materials. Triazines are also known to be useful as electron transporting materials.

Other Useful Organic Layers and Device Architecture

In some instances, layers 109 through 111 can optionally be collapsed into a single layer that serves the function of supporting both light emission and electron transportation. Layers 110 and 111 may also be collapsed into a single layer that functions to block holes or excitons, and supports electron transportation. It also known in the art that emitting materials may be included in the hole-transporting layer, which may serve as a host. Multiple materials may be added to one or more layers in order to create a white-emitting OLED, for example, by combining blue- and yellow-emitting materials, cyan- and red-emitting materials, or red-, green-, and blue-emitting materials. White-emitting devices are described, for example, in EP 1 187 235, US 20020025419, EP 1 182 244, U.S. Pat. Nos. 5,683,823, 5,503,910, 5,405,709, and 5,283,182 and can be equipped with a suitable filter arrangement to produce a color emission.

This invention may be used in so-called stacked device architecture, for example, as taught in U.S. Pat. Nos. 5,703,436 and 6,337,492.

Deposition of Organic Layers

The organic materials mentioned above are suitably deposited by any means suitable for the form of the organic materials. In the case of small molecules, they are conveniently deposited through sublimation, but can be deposited by other means such as from a solvent with an optional binder to improve film formation. If the material is a polymer, solvent deposition is usually preferred. The material to be deposited by sublimation can be vaporized from a sublimator "boat" often comprised of a tantalum material, e.g., as described in U.S. Pat. No. 6,237,529, or can be first coated onto a donor sheet and then sublimed in closer proximity to the substrate. Layers with a mixture of materials can utilize separate sublimator boats or the materials can be pre-mixed and coated from a single boat or donor sheet. Patterned deposition can be achieved using shadow masks, integral shadow masks (U.S. Pat. No. 5,294,870), spatially-defined thermal dye transfer from a donor sheet (U.S. Pat. Nos. 5,688,551, 5,851,709 and 6,066,357) and inkjet method (U.S. Pat. No. 6,066,357).

Encapsulation

Most OLED devices are sensitive to moisture or oxygen, or both, so they are commonly sealed in an inert atmosphere such as nitrogen or argon, along with a desiccant such as alumina, bauxite, calcium sulfate, clays, silica gel, zeolites, alkaline metal oxides, alkaline earth metal oxides, sulfates, or metal halides and perchlorates. Methods for encapsulation and desiccation include, but are not limited to, those described in U.S. Pat. No. 6,226,890. In addition, barrier layers such as SiOx, Teflon, and alternating inorganic/polymeric layers are known in the art for encapsulation.

Optical Optimization

OLED devices of this invention can employ various well-known optical effects in order to enhance its properties if desired. This includes optimizing layer thicknesses to yield maximum light transmission, providing dielectric mirror structures, replacing reflective electrodes with light-absorbing electrodes, providing anti-glare or anti-reflection coatings over the display, providing a polarizing medium over the display, or providing colored, neutral density, or color-conversion filters over the display. Filters, polarizers, and anti-glare or anti-reflection coatings may be specifically provided over the cover or as part of the cover.

The invention and its advantages can be better appreciated by the following examples.

EXAMPLES

Triplet Energy Calculation Example 1

The triplet energy of compound Inv-1 was calculated using the B3LYP method as implemented in the Jaguar computer code (Schrodinger, Inc., Portland Oreg.). The MIDI! basis set was used for H, C, and O atoms. The LACV3P basis set and pseudopotential were used for all transition metal atoms. The energies of the ground state, E(gs), and the lowest triplet state, E(ts), were calculated. The energy of each state was computed at the minimum-energy geometry for that state. The difference in energy between the two states was further modified by the following equation to give the triplet energy: $E(t)=0.84*(E(ts)-E(gs))+0.35$. This procedure was repeated for the remaining compounds listed in Table 1. The triplet energies in eV and the wavelength which corresponds to the 0-0 transition ($\lambda_{0-0}$) are given in Table 1.

TABLE 1

| | Calculated Triplet Energies | |
|---|---|---|
| Compound | Calculated E(t) (eV) | Calculated $\lambda_{0-0}$ (nm) |
| Inv-1 | 2.07 | 593 |
| Inv-2 | 2.08 | 596 |
| Inv-12 | 2.12 | 586 |
| Inv-14 | 2.95 | 420 |
| Inv-15 | 2.96 | 418 |

As can be seen from the Table, complexes of the invention offer a wide range of hues.

Synthetic Example 1

Preparation of 9,9-diphenylfluorene

α,α-Diphenyl-2-biphenylmethanol was prepared by the following procedure (Reaction Scheme 1). To a solution of 2-bromobiphenyl (5.00 g, 21.45 mmol) in freshly distilled THF (50 mL) at −78° C. was added n-BuLi (1.37 g, 21.45 mmol, 8.6 mL of 2.5 M solution in hexanes) dropwise via syringe. Approximately 5 minutes after complete addition, benzophenone (4.10 g, 22.52 mmol) was added in a single portion, after which time the ice bath was removed and the solution allowed to warm to room temperature. After 2 h, the reaction was quenched with the addition of $NH_4Cl$ and $H_2O$ (100 mL), and extracted with $Et_2O$ (3×100 mL). The combined organic layers were washed with brine, dried over $MgSO_4$, and concentrated to dryness. Chromatography gave the product as a white solid (6.27 g, 87% yield).

α,α-diphenyl-2-biphenylmethanol can also be prepared by the following procedure. To a solution of phenylmagnesium bromide (5.26 g, 29.03 mmol, 29 mL of 1.0 M solution in tetrahydrofuran) under $N_2$, was added a solution of 2-benzoylbiphenyl (5.00 g, 19.36 mmol) as a solution in freshly distilled THF (40 mL). After 17 h, the deep purple mixture was quenched with saturated aqueous $NH_4Cl$ (100 mL) and extracted with $Et_2O$ (3×100 mL). The combined organic layers were washed with brine, dried over $MgSO_4$, and concentrated to dryness. Chromatography gave the product as a tacky solid (3.59 g, 55% yield).

9,9-diphenylfluorene was prepared from α,α-diphenyl-2-biphenylmethanol by the following method. To a solution of the starting carbinol (0.50 g, 1.49 mmol) in $CH_2Cl_2$ (10 mL) was added trifluoroacetic acid (10 mL). After refluxing for 1 hour, the reaction was cautiously neutralized by the addition of aqueous $NaHCO_3$. The mixture was then extracted with $Et_2O$ (2×100 mL) that was subsequently washed with additional $H_2O$ (100 mL) and brine, dried over MgSO4 and concentrated to white solid (0.47 g, 99% yield).

Synthetic Example 2

Preparation of Inv-1

The complex Inv-1 (9-[Ph-W(CO)$_3$]-9-phenylfluorene) was prepared by refluxing a reaction mixture of W(CO)$_6$ (1.75 g, 4.97 mmol) and 9,9-diphenylfluorene (1.55 g, 4.87 mmol) under argon in dibutyl ether. The reaction vessel was left open to a bubbler connected to the argon source to allow

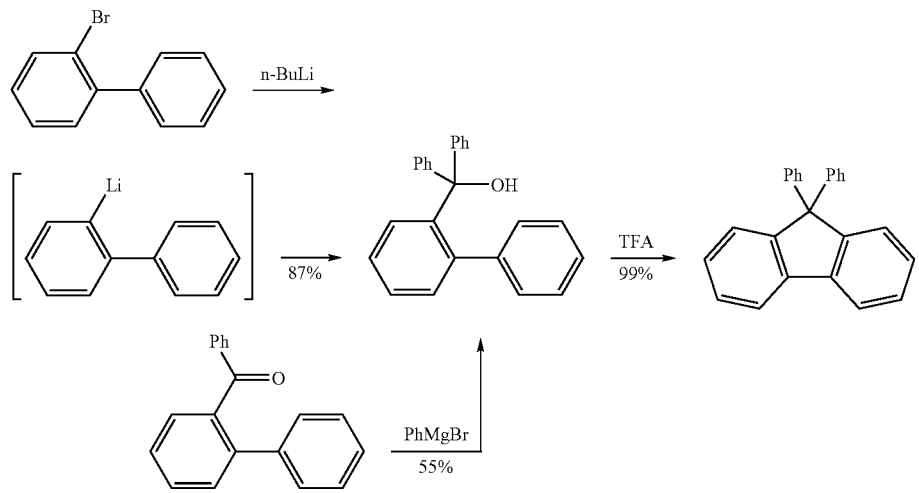

Reaction Scheme 1

CO produced during the reaction to escape. After refluxing the reaction mixture for 16 h, the heat was removed and the solution filtered through a fine porosity glass frit. A yellow solid was isolated after removing the solvent in vacuo. The yellow solid was characterized as a mixture of 9,9-diphenylfluorene and the arene complex 9-[Ph-W(CO)$_3$]-9-phenylfluorene. The tungsten complex was characterized by using H$^1$NMR spectroscopy and Mass Spectrometry. The experimental mass spectrum of the tungsten complex was consistent with the theoretical isotope pattern for the formulation 9-[Ph-W(CO)$_3$]-9-phenylfluorene centered at Mass 587 for positive ion detection.

Room temperature emission spectra were generated from a THF solution of Inv-1. The THF solution of the tungsten complex was prepared in an argon drybox. The solution was excited at 300 nm using a Luminance Spectrometer resulting in two strong emission bands at 627 and 684 nm.

Prophetic Device Example 1

An EL device satisfying the requirements of the invention is constructed in the following manner:
1. A glass substrate is coated with an 85 nm layer of indium-tin oxide (ITO) as the anode is sequentially ultrasonicated in a commercial detergent, rinsed in deionized water, degreased in toluene vapor and exposed to oxygen plasma for about 1 min.
2. Over the ITO is deposited a 1 nm fluorocarbon (CFx) hole-injecting layer (HIL) by plasma-assisted deposition of CHF$_3$.
3. A hole-transporting layer (HTL) of N,N'-di-1-naphthyl-N,N'-diphenyl-4,4'-diaminobiphenyl(NPB) having a thickness of 75 nm is then evaporated from a tantalum boat.
4. A 35 nm light-emitting layer (LEL) of 4,4'-N,N'-dicarbazole-biphenyl (CBP) and Inv-1 (4% wt %) is then deposited onto the hole-transporting layer. These materials are also evaporated from tantalum boats.
5. A hole-blocking layer of bis(2-methyl-quinolinolate)(4-phenylphenolate) (Al (Balq)) having a thickness of 10 nm is then evaporated from a tantalum boat.
6. A 40 nm electron-transporting layer (ETL) of tris(8-quinolinolato)aluminum (III) (AlQ$_3$) is then deposited onto the light-emitting layer. This material is also evaporated from a tantalum boat.
7. On top of the AlQ$_3$ layer is deposited a 220 nm cathode formed of a 10:1 volume ratio of Mg and Ag.

The above sequence completes the deposition of the EL device. The device is then hermetically packaged in a dry glove box for protection against ambient environment.

Upon operation of the device, holes are injected at the anode and electrons are injected at the cathode. Recombination of these charges takes place near the interface between the HTL and the LEL, forming excited states. Some excited states may form directly on Inv-1. Excited states not formed directly on Inv-1 efficiently move via Förster or Dexter energy transfer onto Inv-1. Once on Inv-1, excited states efficiently emit via phosphorescence.

The entire contents of the patents and other publications referred to in this specification are incorporated herein by reference. The invention has been described in detail with particular reference to certain preferred embodiments thereof, but it will be understood that variations and modifications can be effected within the spirit and scope of the invention.

| PARTS LIST | |
|---|---|
| 101 | Substrate |
| 103 | Anode |
| 105 | Hole-Injecting layer (HIL) |
| 107 | Hole-Transporting layer (HTL) |
| 109 | Light-Emitting layer (LEL) |
| 110 | Hole-blocking layer (HBL) |
| 111 | Electron-Transporting layer (ETL) |
| 113 | Cathode |

What is claimed is:

1. An electroluminescent device comprising a light-emitting layer containing a light emitting phosphorescent material that contains an organometallic complex comprising a metal selected from the group consisting of Mo, W, Re, Ru, and Os that is coordinated to a neutral or negatively-charged ligand group through the π electrons of the ligand with a hapticity greater than 2 wherein the light-emitting layer contains a light emitting compound of Formula (1),

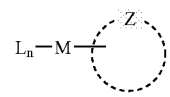

(1)

wherein:
M represents Mo, W, Re, Ru, or Os,
Z represents the atoms necessary to form a ligand group that is neutral or negatively charged and Z is coordinated to M though π electron density with a hapticity greater than 2;
L represents independently selected ligand groups, provided that L is chosen so as to create a neutral complex with 18 electrons in the valence shell of M; and
n is 1-4, as necessary to fulfill the requirements of a neutral complex with 18 electrons in the valence shell of M provided that Z is represented by Formula (2),

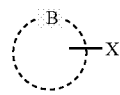

(2)

wherein:
B represents the atoms necessary to complete a 5- or 6-membered aromatic ring group that is complexed to M through π electron density on B; and
X represents a substituent group that comprises a conjugated system.

2. The device of claim 1 wherein the ligand group comprises an aromatic system and donates 6 π electrons.

3. The device of claim 1 wherein the ligand group is selected from the group consisting of a phenyl group and a η$^5$-cyclopentadienyl group.

4. The device of claim 1 wherein the ligand is substituted with a group that comprises a conjugated system.

5. The device of claim 1 wherein the ligand is substituted with an aromatic group.

6. The device of claim 1 wherein the ligand is substituted with a fluorene group.

7. The device of claim 1 wherein the metal is W.

8. The device of claim 1 wherein the metal is Re.

9. The device of claim 1 wherein the light emitted from the light-emitting layer has maximum intensity at a wavelength between 600 and 700 nm.

10. The device of claim 1 wherein the light emitted from the light-emitting layer has maximum intensity at a wavelength between 500 and 600 nm.

11. The device of claim 1 wherein the light emitted from the light-emitting layer has maximum intensity at a wavelength between 400 and 500 nm.

12. The device of claim 1 wherein M represents W, Re or Os.

13. The device of claim 1 wherein M represents W.

14. The device of claim 1 wherein M is W, L is carbon monoxide and n is 3.

15. The device of claim 1 wherein M is W, L is carbon monoxide, n is 3, and Z is a 9,9-diphenylfluorene group.

16. The device of claim 1 wherein Z represents the atoms necessary to complete a 5- or 6-membered aromatic ring group.

17. The device of claim 1 wherein Z represents the atoms necessary to complete a phenyl group or a $\eta^5$-cyclopentadienyl group.

18. The device of claim 1 wherein M is Re, L is carbon monoxide, n is 3, and Z is a $\eta^5$-cyclopentadienyl group.

19. The device of claim 1 wherein Z comprises a fluorene group.

20. The device of claim 1 wherein X is conjugated with B.

21. The device of claim 1 wherein X is not conjugated with B.

22. The device of claim 1 wherein the light-emitting material is a phosphorescent material compound disposed in a host material.

23. The device of claim 22 containing the phosphorescent material compound, in an amount of up to 15 wt % based of the host.

24. The device of claim 1 wherein the light-emitting material is part of a polymer.

25. The device of claim 1 including a means for emitting white light.

26. The device of claim 1 including a light filter.

27. The device of claim 1 including a fluorescent emitting material.

28. A display comprising the electroluminescent device of claim 1.

29. An area lighting device comprising the electroluminescent device of claim 1.

30. A process for emitting light comprising applying a potential across the device of claim 1.

31. A composition of matter comprising a tungsten tricarbonyl compound given by Formula (3),

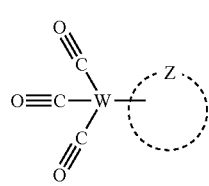

(3)

wherein:

Z is chosen from the group consisting of 9,9-diphenylfluorene, 9-phenyl-9-alkylfluorene, and o-terphenyl groups.

32. The device of claim 1 wherein the organometallic complex is represented by formula 4A, 4B, or 4C:

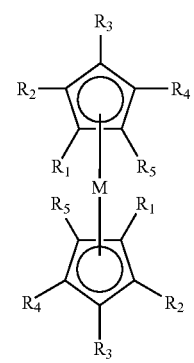

4A

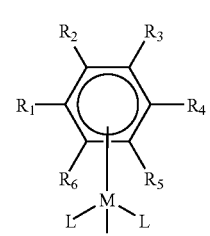

4B

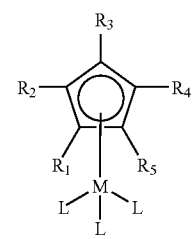

4C wherein each M is Os, Ru, Re, Mo, or W, each $R^1$-$R^6$ group is bonded to an aromatic ring coordinating to the metal and is independently H or a substituent with at least one such R group being a substituent conjugated with the coordinating aromatic ring; and each L represents an independently selected ligand group, provided that L is chosen so as to create a neutral complex with 18 electrons in the valence shell of M;

33. The device of claim 32 wherein the organometallic complex is represented by formula 4A or 4C and M is Os or Ru.

34. The device of claim 33 wherein M is Os.

35. The device of claim 32 wherein the organometallic complex is represented by formula 4B and M is W or Mo.

36. The device of claim 32 wherein the organometallic complex is represented by formula 4C and M is Re.

37. The device of claim 32 wherein at least one R group is an alkenyl or aryl group.

38. The device of claim 32 wherein at least one R group is an aryl group.

39. The device of claim 32 wherein at least one R group is selected from phenyl, naphthyl, anthryl, biphenyl, and alkenyl groups.

40. The device of claim 32 wherein at least one R group is selected so as to form a bis compound containing two M atoms.

41. The device of claim 32 wherein the organometallic complex is represented by formula 4A.

42. The device of claim 32 wherein the organometallic complex is represented by formula 4B.

43. The device of claim 32 wherein the organometallic complex is represented by formula 4C.

44. The device of claim 34 wherein at least one L group is a —C≡O group.

* * * * *